United States Patent [19]

Sherva-Parker

[11] Patent Number: 4,547,912
[45] Date of Patent: Oct. 22, 1985

[54] AMPUTATION APPARATUS

[76] Inventor: Carole J. Sherva-Parker, 5117 Skylite Dr., Utica, Mich. 48087

[21] Appl. No.: 528,429

[22] Filed: Sep. 1, 1983

[51] Int. Cl.[4] ............ A61F 1/04; A61F 1/06; A61F 1/02
[52] U.S. Cl. .................. 623/16; 128/92 C; 623/57; 623/58
[58] Field of Search ............ 3/1, 1.9, 1.91, 2, 12, 3/12.1, 17, 18, 19, 21; 128/92 C, 92 CA

[56] References Cited

U.S. PATENT DOCUMENTS

| | | | |
|---|---|---|---|
| 2,578,019 | 12/1951 | Ryan | 3/3 |
| 3,186,006 | 6/1965 | Miller | 3/19 |
| 3,808,606 | 5/1974 | Tronzo | 3/1 |
| 3,947,897 | 4/1976 | Owens | 3/12 |
| 3,979,779 | 9/1976 | Zeibig, et al. | 3/1.91 |
| 4,007,494 | 2/1977 | Saver | 128/92 C |
| 4,007,495 | 2/1977 | Frazier | 3/1.91 |
| 4,041,550 | 8/1977 | Frazier | 3/1.91 |
| 4,085,466 | 4/1978 | Goodfellow et al. | 3/1.91 |
| 4,158,895 | 6/1979 | Reswick et al. | 3/12 |
| 4,180,873 | 1/1980 | Fixel | 3/1.912 |
| 4,206,517 | 6/1980 | Pappas et al. | 3/1.91 |
| 4,281,419 | 8/1981 | Treace | 3/1.9 |

Primary Examiner—Richard J. Apley
Assistant Examiner—David J. Isabella
Attorney, Agent, or Firm—Basile, Weintraub & Hanlon

[57] ABSTRACT

Amputation apparatus for use with an internal prosthesis attachable to the end of a stump having an outwardly extending bone. The amputation apparatus includes a cap having an internal cavity for insertion over the bone and an opposed outwardly extending boss. A plate having an internal cavity is mountable over the outwardly extending boss of the cap. The plate has a radial extent substantially greater than the radial extent of the cap to define an equal weight distribution surface for internal and external forces over the entire bottom surface of the stump.

15 Claims, 6 Drawing Figures

AMPUTATION APPARATUS

BACKGROUND OF THE INVENTION

1. Field of the Invention

This invention relates, in general, to prostheses which are externally attachable to severed or amputated limbs and, more specifically, to apparatus for use in attaching prostheses to limbs.

2. Description of the Prior Art

It is common to attach a prosthesis or artificial limb externally onto a limb of an individual which has been amputated or otherwise severed in order to provide a measure of use of the limb to the individual. Typically, a strap and harness assembly is utilized which engages the stump of the limb. During use of the weight bearing limb, such as a leg or arm, forces are generated which are transmitted through the prosthesis directly to the flesh surrounding the stump. Since it is difficult to insure a secure, non-slip engagement between the prosthesis and the stump, the forces generated during use of the prosthesis create movement of the prosthesis relative to the stump which results in irritation of the flesh surrounding the stump and discomfort to the wearer which makes it difficult, if not impossible, to effectively use the prosthesis in a normal manner.

One solution to the above-listed problems is set forth in U.S. Pat. No. 3,947,897. In this device, a socket is inserted directly into a cavity of the bone at the end of the stump. The prosthesis is contoured to the shape of the stump and includes a lock pin insertable within the socket for releasably mounting the prosthesis to the socket and stump.

As shown in U.S. Pat. Nos. 2,578,019 and 3,186,006, it has also proposed to employ cushions or pads which are disposed between the end of the stump and the prosthesis to absorb and cushion some of the forces and pressures transmitted from the prosthesis to the stump.

While the above-described devices reduce to a certain extent some of the forces transmitted to the stump and thereby ease some of the discomfort typically encountered with the use of a prosthesis, such devices fail to evenly distribute the forces over the entire end of the stump such that directional forces still cause pressures to be exerted on the stump resulting in discomfort to the user.

Thus, it would be desirable to provide an amputation apparatus which overcomes the problems of previously devised devices for use with a prosthesis attached externally to a severed or amputated limb. It would also be desirable to provide an amputation apparatus which evenly distributes the forces exerted by the prosthesis over the end of the stump to reduce the discomfort caused by such forces. Finally, it would be desirable to provide an amputation apparatus which is available in a variety of sizes for use on different size individuals, from adults to children, and also to allow for bone and/or flesh growth and changes in the shape and size of the limb itself.

SUMMARY OF THE INVENTION

The present invention is an amputation apparatus for use with an external prosthesis attachable to the end of a severed limb or stump. The amputation apparatus includes a cap having first and second ends, with a cavity formed in the first end and a boss or projection extending outwardly from the second end. The cavity in the first end of the cap is insertable over the end of the bone in the stump and secured thereto, preferably by use of a bio-compatible adhesive.

A plate has a top and bottom surfaces, with a cavity formed in the top surface which is interconnectable with the plug or boss on the cap. A bio-compatible adhesive is utilized to secure the interconnected plug and cavity together so as to securely mount the plate on the cap. The plate is shaped with an outer periphery, either circular or oval in configuration, which has a substantially greater radius than the radius of the outer periphery of the cap.

With the plate securely mounted on the cap, a loose strip of skin or skin and muscle is pulled over and wrapped about the bottom surface of the plate and sutured to the opposite side of the stump. A cinch strap is secured about the stump above the plate. A bandage basket is also mounted over the stump during the healing of the skin tissue.

In an alternate embodiment, the amputation apparatus of the present invention is adapted for use on pre-adult individuals in which subsequent bone and tissue growth will occur. In this embodiment, the amputation apparatus is removably secured to a mesh member which is sutured to the muscle proximal the end of the stump. In this manner, the cap and plate assembly may be removed and replaced with a larger size cap and plate assembly when bone and tissue growth occurs.

The amputation apparatus of the present invention overcomes many of the problems encountered with previously devised apparatus and methods for attaching prosthesis to stumps. The amputation apparatus of the present invention uniquely distributes forces and pressures transmitted from the prosthesis during its use to the stump in an equal manner over the entire bottom surface of the stump. Furthermore, the amputation apparatus distributes body weight pressure evenly across the stump thus preventing internal stump damage cause by limb and/or body weight pressure being borne solely on the bone end. The plate and cap prevent contact between the bone end and the surrounding tissue thereby preventing tissue damage caused by grinding of the bone end into the tissue. This provides greater comfort for the user of the prosthesis and prevents irritation of the flesh surrounding the stump during use of the prosthesis.

BRIEF DESCRIPTION OF THE DRAWING

The various features, advantages and other uses of the present invention will become more apparent by referring to the following detailed description and drawing in which.

DESCRIPTION OF THE PREFERRED EMBODIMENTS

Figure 1:
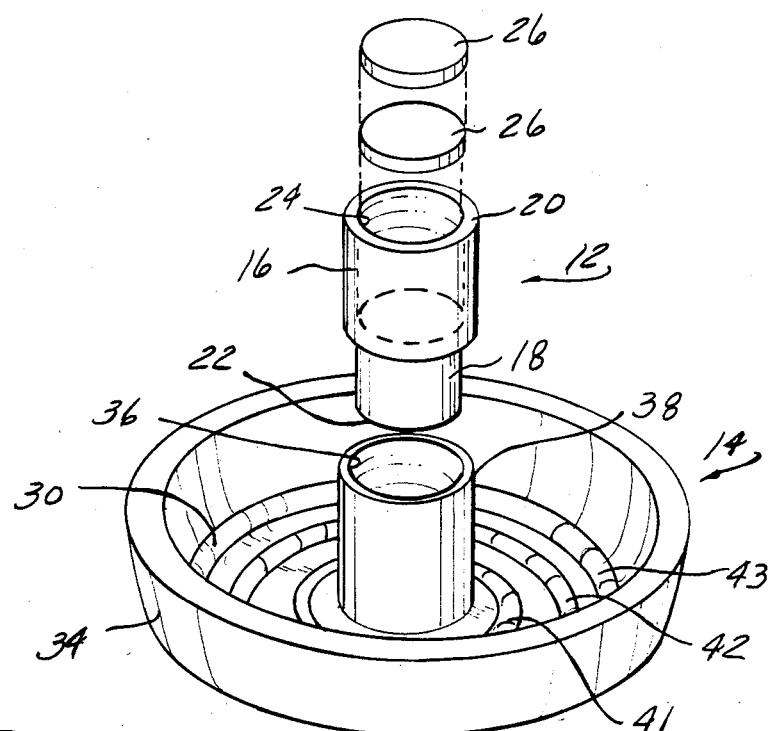
FIG. 1 is an exploded, perspective view of an amputation apparatus constructed in accordance with the teachings of the present invention.

Throughout the following description and drawing, an identical reference number is used to refer to the same component shown in multiple figures of the drawing.

Referring now to the drawing, there is illustrated an amputation apparatus 10 which is used with a prosthesis mountable externally on the end of a stump of a severed or amputated limb to evenly distribute forces transmitted by the prosthesis across the stump and internally through the bone end.

As shown in FIG. 1, the amputation apparatus 10 includes a cap 12 and a plate 14. The cap is formed of a body member constructed of a neutral, bio-compatible material. The cap 12 typically has a circular cross-section and is formed with first and second portions 16 and 18, respectively, having different cross-sections or diameters. The cap 12 is also provided with first and second opposed ends 20 and 22, respectively.

A recess or internal cavity 24 is formed in the first end 20 of the first portion 16 of the cap 12. The cavity 24 extends partially through the first portion 16 of the cap 12, as shown in FIG. 1 and, preferably, has a circular cross-section.

The second portion 18 of the cap 12, which has a smaller diameter or cross-section than that of the first portion 16 of the cap 12, defines a boss or projection which extends outward from the end of the first portion 16 of the cap 12. The outer end of the second portion or boss 18 defines the second end 22 of the cap 12.

The cap 12 of the present invention may be formed in a variety of sizes, corresponding to minimal O.D. so as to enable its use on a variety of different sized individuals and to allow removal and exchange of the cap 12 for bone and tissue growth during the life of the user. Furthermore, the boss 18 and cavity 24 may have different diameters than that illustrated in FIG. 1 to accomodate varying plate sizes, described hereafter, as well as different stump diameters.

As shown in FIG. 1, a plurality of elevator members 26 are removably insertable within the cavity 24 within the cap 12. The elevator members 26 are circular discs having a cross-section equal to the cross-section of the cavity 24. Any number of elevators 26 may be inserted within the cavity 24 in the cap 12 to permit variation in the attachment of the cap 20 on the end of the bone of the stump, as described and illustrated hereafter.

The amputation apparatus 10 of the present invention also includes a plate 14 in the form of a thin body formed of a neutral, bio-compatible material. The plate 14 is formed with opposed, top and bottom surfaces 30 and 32, respectively. Preferably, the plate has a cup-like configuration including an upwardly extending side wall 34. Preferably, the side wall 34 is formed with rounded or smooth corners to prevent tissue damage when the plate 14 is mounted on the end of a stump of a severed or amputated leg.

As shown in FIG. 1, the radial extent of the periphery of the plate 14 is substantially greater than the corresponding radial extent of the periphery of the cap 12 such that the side wall 34 of the plate 14 extends a substantial radial distance outward beyond the outer peripheral surface of the cap 12 so as to define a large weight bearing surface. The plate 14 may be formed in any desired configuration, although circular or oval configurations are preferred.

A cavity or recess 36 is formed in the plate 14 and has a diameter which mates with the boss 18 on the cap 12 so as to sungly be inserted over the periphery of the boss 18.

Figure 2:
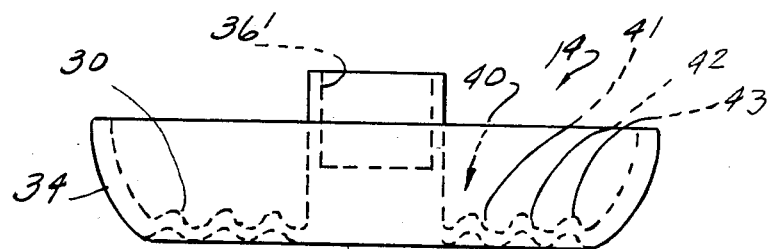
FIG. 2 is a side elevational view of another embodiment of the plate utilized in the amputation apparatus of the present invention.
Figure 3:
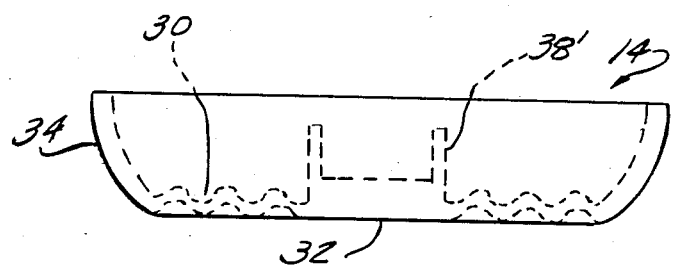
FIG. 3 is a side elevational view of yet another embodiment of the plate utilized in the amputation apparatus of the present invention.
Figure 4:
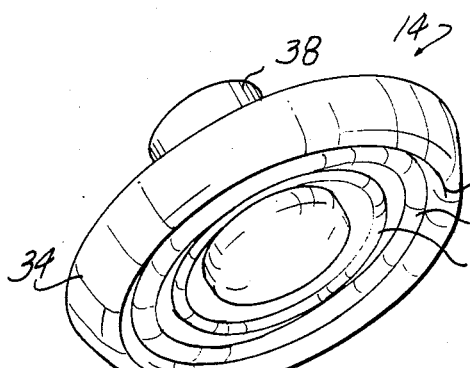
FIG. 4 is a perspective view of the bottom of the plate utilized in the amputation apparatus of the present invention showing the construction of the spaced ribs.

In the embodiments shown in FIGS. 1 and 2, a second boss or projection 38 is formed integrally with and extends upward from the top surface 30 of the plate 14 above the upper end of the side wall 34. The internal cavity 36 is formed within the boss 38 and, in one embodiment shown in FIG. 1, extends through a portion of the depth of the boss 38. In a second embodiment illustrated in FIG. 2, the internal cavity 36' extends through the entire length of the boss 38 into the interior of the plate 14. Alternately, as shown in FIG. 3, the boss 38' may extend upward only a portion of the height of the side wall 34 of the plate 14.

As shown in FIGS. 1-4, rib means 40 are formed on the plate 14. The rib means 40 functions to provide a holding surface for the surrounding skin and tissue after the plate 14 is installed upon an end of a stump to securely hold the plate 14 in position on the end of the stump and to provide space for post-operative tissue swelling.

In a preferred embodiment, the rib means 40 comprises a plurality of concentric, annular ribs, such as ribs 41, 42 and 43, which are integrally formed on the plate 14. As shown in FIGS. 1-4, the ribs 41, 42 and 43 comprises corrugations formed in the plate 14 which encircle the boss 38. Alternately, the rib means 40 may comprise a plurality of annular flanges mounted on the top and/or bottom surfaces 30 and 32 of the plate 14.

Figure 5:
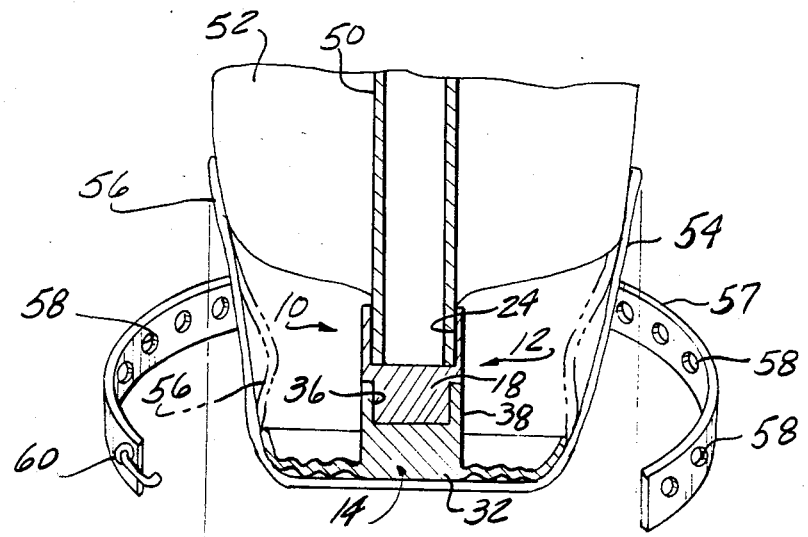
FIG. 5 is an exploded, partially sectioned view showing the mounting of the amputation apparatus of the present invention externally on the end of a stump.
Figure 5:
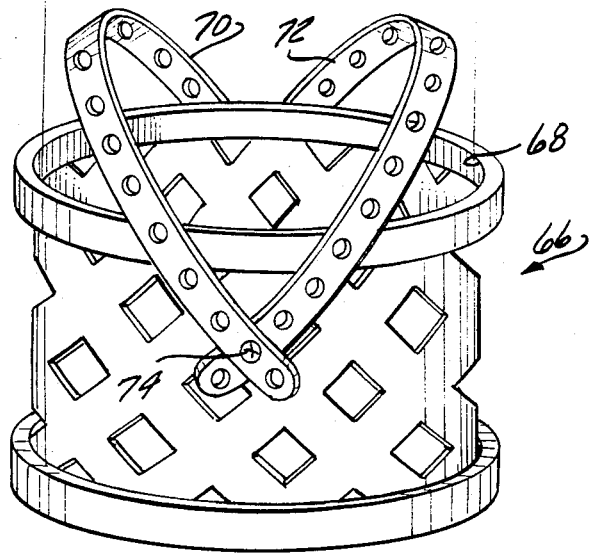

As shown in FIG. 5, the amputation apparatus 10 of the present invention is adapted to be disposed over and connected to the end of the bone 50 located at the end of a stump 52 of a severed or amputated limb. The cap 12 is inserted directly over the end of the exteriorally extending, exposed portion of the bone 50 with the internal cavity 24 formed in the first end 20 of the cap 12 snugly engaging the bone 50.

Securing means, such as a bio-compatible adhesive, is disposed between the mating surfaces of the cavity 24 and the bone 50 so as to securely mount the cap 12 of the end of the bone 50.

The plate 14 is then mounted directly on the outwardly extending plug or boss 18 on the cap 12. In so doing, the internal cavity 36 on the plate 14 is disposed directly over the plug or boss 18 on the cap 12 and secured thereto by a suitable adhesive. In this way, the cap 12 and plate 14 are securely mounted on the bone 50.

Prior to the installation of the amputation apparatus 10 of the present invention on the end of a bone on a stump, the stump 50 is prepared for attachment of the amputation apparatus 10. An incision is made through the skin which is separated from the muscles and peeled back to a point approximately two times the diameter of the plate 14 above the end of the bone 50. The muscles are then excised around the bone 50 and the bone end itself is cleaned. The cap 12 is then mounted in position and bonded to the end of the bone 50. Next, the plate 14 is securely mounted to the cap 12, as described above.

The skin 54 from one side of the stump 52 is then brought down and across the bottom surface 32 of the plate 14 and up to the opposed side 56 of the stump 52.

The skin portion 54 may be selected from either the front or back of the stump 52, as well as from either the left or right sides of the stump 52.

A cinch strap 57 in the form of an elongated strip member is secured about the stump 52 above the plate 14. The cinch strap 57 draws the skin in around the bone 50 and the cap area, as shown in phantom in FIG. 5, to facilitate the attachment of an external device or prosthesis. Any excess skin folds created by the cinching may be surgically excised to further enhance the fit of an external device and/or prosthesis.

As shown in FIG. 5, a bandage basket 66 containing bandages, or to hold bandages not shown, disposed about the stump 52 is then mounted over the end of the stump 52. The bandage basket 66 is formed of a flexible, large-opening, weaved container having an open top end 68. The configuration or cross-section of the bandage basket 68 is compatible with that of the plate 14 and may be either circular or oval in cross-section. Two flexible hanger straps 70 and 72 mounted on the basket 66 are criss-crossed in front of the basket 66 and interconnected by means of a pin 74 attached to the bandage basket 66, to securely hold the basket 66 in position on the stump 52 during the skin and tissue healing process.

After the skin has properly healed, the bandage basket 66 and cinch strap 57 are removed from the stump 52 and a suitable prosthesis or other external device, not shown, can then be mounted on the stump 52.

During use of the prosthesis, the plate 14, which defines a large weight bearing surface at the end of the bone 50 of the stump 52, will evenly distribute forces transmitted by the prosthesis over the entire bottom surface of the bone 50 and the stump 52. This has the effect of equally distributing such forces so as to prevent any internal or external directional forces from being urged on the stump 52 which could cause discomfort to the user.

Figure 6:
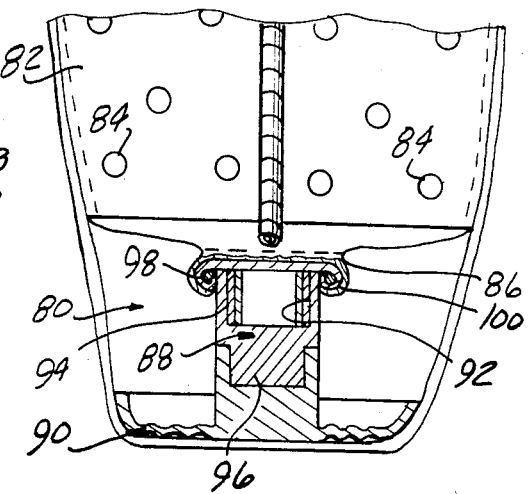
FIG. 6 is a partial, exploded view showing the mounting of another embodiment of the amputation apparatus of the present invention on the end of a stump of a pre-adult.

Referring now to FIG. 6, there is illustrated an alternate embodiment of the amputation apparatus of the present invention. In this embodiment, the amputation apparatus 80 is shown mounted on the end of the stump of a pre-adult individual in which future bone and tissue growth will occur. The amputation apparatus 80 includes a member 82 formed of a mesh-like material which is sutured to the muscle surrounding the end of the stump. An outer layer 85 is provided on the mesh member 82 and includes a hole pattern 84 which provides a location for sutures used to attach the mesh member 82 to the muscle.

The mesh member 82 includes a lower centrally located depending portion 86 which is adapted to releasably receive the cap thereon, as described hereafter.

The amputation apparatus 80 also includes a cap 88 and a plate 90. The cap 90 is formed of a suitable biocompatible metallic material and has a circular cross-section with a first recess or cavity 92 formed at an upper end. A layer of a compressable material 94 is disposed interiorally within the first recess 92 and is adapted to surround and engage the end of the bone of the stump. A boss or projection 96 is formed on the second end of the cap 88 for receiving the plate 90 thereon, in the same manner as described and illustrated above for the amputation apparatus 10.

The plate assembly 90 is identically formed as that illustrated in FIG. 1 such that a detailed description will not now be provided. It will be understood, however, that the plate 90 is secured to the boss 96 on the cap 88 by means of an adhesive as described above.

The cap 88 is releasably secured to the bottom end 86 of the mesh member 82 by means of a cable connector 98 which is releasably insertable into arcuate, depending figures 100 formed at the upper end of the cap 88. Insertion of the cable connector 98 within the interior of the depending figures 100 secures the cap 88 to the depending end 86 of the mesh member 82 to thereby securely and releasably mount the amputation apparatus 80 of the present invention on the end of the bone of the stump. When bone and tissue growth occurs the cable 98 may be removed so as to detach the plate 90 and cap 88 from the end of the bone of the stump and allow the installation of a larger sized cap and plate assembly.

In summary, there has been disclosed an unique amputation apparatus which evenly distributes internal and external forces across the entire bottom surface of a stump. The amputation apparatus of the present invention is easily installed and secured on the end of the bone in the stump. The amputation apparatus of the present invention may, also, be provided in a variety of sizes so as to enable its application on many different size individuals, as well as replacement to allow for bone and tissue growth.

What is claimed is:

1. An amputation apparatus for use with a prosthesis attachable externally to a stump having a bone, the amputation apparatus comprising:
   a cap securable to the end of the bone in the stump, the cap having an open top, a bottom and side walls sized to fit externally over the end of the bone; and
   a plate disposable completely internally within the stump and attachable to the cap, the plate extending radially outward a substantial distance beyond the outer periphery of the cap to define a large weight bearing surface at the end of the bone to evenly distribute forces over the entire end of the stump.

2. The amputation apparatus of claim 1 further including:
   means for interconnecting the cap and the plate,
   the interconnecting means comprising mating interconnecting portions formed on the cap and the plate; and
   means for securing the mating portions of the cap and plate together.

3. The amputation apparatus of claim 2 wherein the means for securing the mating portions of the cap and plate together comprises adhesive means.

4. The amputation apparatus of claim 2 wherein:
   the bottom of the cap is formed as an outwardly extending boss; and
   an internal cavity is centrally formed within the plate and adapted to be disposed externally over the outwardly extending boss on the cap.

5. The amputation apparatus of claim 4 wherein the boss on the cap and the internal cavity in the plate have matingly formed circular cross-sections.

6. The amputation apparatus of claim 4 wherein the plate includes a centrally located boss extending upward from the plate, the plate boss having the internal cavity formed therein.

7. The amputation apparatus of claim 1 wherein the plate has a circular cross-section.

8. The amputation apparatus of claim 1 wherein the plate has an oval configuration.

9. The amputation apparatus of claim 1 further including:
   rib means formed integral in the plate.

10. The amputation apparatus of claim 9 wherein the rib means comprises at least one annular rib.

11. The amputation apparatus of claim 9 wherein the rib means comprises a plurality of concentric corrugations formed in the plate.

12. An amputation apparatus for use with an external prosthesis attachable to a stump having a bone, the amputation apparatus comprising:

a cap having first and second portions, the second portion having a smaller diameter than the first portion which defines an outwardly extending boss on the cap, an internal cavity formed in the cap sized to fit externally over the end of the bone;

a plate having top and bottom surfaces and a centrally located boss formed on the top surface, the plate extending radially outward a substantial distance beyond the periphery of the cap to evenly distribute forces from the prosthesis over the end of the stump, the plate being disposed completely internally within the stump;

a first cavity formed within the boss on the plate for insertion over the boss on the cap;

first adhesive means for securing the cap and plate together; and second adhesive means for securing the cap on the bone.

13. The amputation of claim 12 further including a plurality of concentric ribs integrally formed on the plate.

14. An amputation apparatus for use with an extenral prosthesis attachable to a stump having a bone, the amputation apparatus comprising:

a mesh member securable to the tissue surrounding the bone at the end of the stump, the mesh member including a depending lower end portion;

a cap having first and second portions, the second portion having a smaller diameter than the first portion which defines an outwardly extending boss on the cap, the cap having an internal cavity formed on the end of the first portion for external insertion about the bone;

a cable connector removably receivable within the depending flanges on the cap to releasably mount the cap on the depending lower end portion of the mesh member; and a plate having top and bottom surfaces and a centrally located boss formed on a top surface, the plate extending radially outward a substantial distance from the periphery of the cap to evenly distribute forces from the prosthesis over the end of teh stump, the plate being disposed completely internally within the stump, a first cavity formed within a boss on the plate for insertion over the boss on the cap; and adhesive means for securing the cap and plate together.

15. The amputation apparatus of claim 17 further including:

a layer of compressible material disposed within the cavity in the cap for surrounding the end of the bone of the stump.

* * * * *